(12) United States Patent
Nakazawa et al.

(10) Patent No.: US 11,352,588 B2
(45) Date of Patent: Jun. 7, 2022

(54) MUSK-LIKE COMPOSITION

(71) Applicant: Kao Corporation, Tokyo (JP)

(72) Inventors: Yuki Nakazawa, Wakayama (JP); Shoji Saito, Wakayama (JP); Misato Sawaguchi, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/045,067

(22) PCT Filed: Apr. 2, 2019

(86) PCT No.: PCT/JP2019/014653
§ 371 (c)(1),
(2) Date: Oct. 2, 2020

(87) PCT Pub. No.: WO2019/194186
PCT Pub. Date: Oct. 10, 2019

(65) Prior Publication Data
US 2021/0163845 A1    Jun. 3, 2021

(30) Foreign Application Priority Data
Apr. 2, 2018    (JP) .............................. JP2018-070661

(51) Int. Cl.
| C11B 9/00 | (2006.01) |
| A61K 8/49 | (2006.01) |
| A61Q 13/00 | (2006.01) |
| C11D 3/50 | (2006.01) |
| D06M 13/228 | (2006.01) |

(52) U.S. Cl.
CPC .......... *C11B 9/0084* (2013.01); *A61K 8/4973* (2013.01); *A61Q 13/00* (2013.01); *C11D 3/50* (2013.01); *D06M 13/228* (2013.01)

(58) Field of Classification Search
CPC ...... C11B 9/0084; A61K 8/4973; A61Q 13/00
See application file for complete search history.

(56) References Cited

U.S. PATENT DOCUMENTS

| 3,681,395 | A |  | 8/1972 | Mookherjee et al. |
| 5,726,328 | A | * | 3/1998 | Mane .................... C07D 313/00 549/266 |
| 6,150,538 | A |  | 11/2000 | Delphis |
| 6,255,276 | B1 | * | 7/2001 | Frater .................... C07D 313/00 512/11 |
| 2016/0089317 | A1 |  | 3/2016 | Cetti et al. |
| 2016/0368888 | A1 |  | 12/2016 | Davey et al. |
| 2017/0211014 | A1 |  | 7/2017 | Hölscher et al. |

FOREIGN PATENT DOCUMENTS

| EP | 0908455 | 4/1999 |
| JP | 11-293284 A | 10/1999 |
| JP | 3040449 | 3/2000 |
| JP | 2014-520103 A | 8/2014 |
| JP | 2016-124868 A | 7/2016 |
| JP | 2017-517477 A | 6/2017 |
| JP | 2017-531468 A | 10/2017 |
| WO | WO 2012/167171 A2 | 12/2012 |
| WO | WO 2015/136093 A1 | 9/2015 |
| WO | WO 2016/005361 A1 | 1/2016 |
| WO | WO 2016/049404 A1 | 3/2016 |
| WO | WO 2016/103677 A1 | 6/2016 |

OTHER PUBLICATIONS

Majee, R.N. et al., "Facile synthesis of (E)-7-hexadecen-1,16-olide (ambrettolide)," Journal of Indian Chemical Society, Nov. 2006, vol. 83, p. 1179-1180 (3 total pages).
Witkowska-Banaszczak, E., "Identification of the components of the essential oil from *Trollius europaeus* flowers," Acta Physiol Plant, 2013, vol. 35, pp. 1421-1425.
Rosebrugh, L.E. et al., "Highly Active Ruthenium Metathesis Catalysts Exhibiting Unprecedented Activity and Z-Selectivity," Journal of The American Chemical Society, 2013, vol. 135, pp. 1276-1279.
Rastogi, S.C. et al., "Fragrances and other materials in deodorants: search for potentially sensitizing molecules using combined GC-MS and structure activity relationship (SAR) analysis," Contact Dermatitis, 1998, vol. 39, pp. 293-303.
Wang, C. et al., "Efficient and Selective Formation of Macrocyclic Disubstituted Z Alkenes by Ring-Closing Metathesis (RCM) Reactions Catalyzed by Mo- or W-Based Monoaryloxide Pyrrolide (MAP) Complexes, applications to Total Syntheses of Epilachnene, Yuzu Lactone, Ambrettolide, Epothilone C and Nakadomarin A," Chemistry, Feb. 18, 2013, vol. 19, No. 8, pp. 1-37.

(Continued)

*Primary Examiner* — Arrie L Reuther
(74) *Attorney, Agent, or Firm* — Oblon, McClelland, Maier & Neustadt, L.L.P.

(57) ABSTRACT

Provided is a musk-like composition that is excellent in harmony with various other fragrances and that can create a distinctive fragrance effect when blended.

The composition includes a compound represented by General Formula (I). The ratio of an E-isomer of the compound represented by General Formula (I) to a Z-isomer of the compound represented by General Formula (I) is E-isomer/Z-isomer=3/7 or more and 7/3 or less.

[Chemical Formula 1]

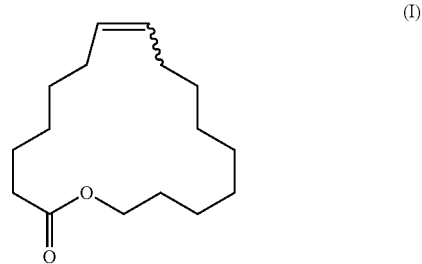

(I)

10 Claims, No Drawings

(56) References Cited

OTHER PUBLICATIONS

Sanz, V. et al., "Synthesis of Ambrettolide from Phloionolic Acid," Journal of Chemical Society, Perkin Transaction 1, 1982, pp. 1837-1839.
International Search Report dated Jun. 11, 2019 in PCT/JP2019/014653 filed on Apr. 2, 2019 citing documents AD, AN, AP, AT, and AV-AX therein, 2 pages.
Extended European Search Report dated Nov. 23, 2021, in EP 19780904.9, 6 pages.

* cited by examiner

MUSK-LIKE COMPOSITION

CROSS REFERENCE TO RELATED APPLICATION

This application is a national stage entry under 35 USC 371 of PCT/JP2019/014653, filed on Apr. 2, 2019, and claims priority to Japanese Patent Application No. 2018-070661 filed on Apr. 2, 2018.

TECHNICAL FIELD

The present invention relates to a musk-like composition.

BACKGROUND ART

Fragrance is an important element that creates, for example, preference, a sense of luxury, a sense of ease, and expectations for the effect of products. Furthermore, a distinctive fragrance provides an effect of identifying products and the capacity for attracting customers. Particularly, musk fragrance notes are used in various formulated fragrances for products such as soaps and cosmetics.

Oxacycloheptadec-10-en-2-one, oxacycloheptadec-8-en-2-one and the like are known as fragrance materials that impart musk fragrance notes to products.

Patent Document 1 discloses the production of oxacycloheptadec-10-en-2-one (isoambrettolide) having an E-isomer:Z-isomer ratio of 85:15.

Patent Document 2 discloses the production of oxacycloheptadec-10-en-2-one containing a Z-isomer in an amount of 99.5% or more.

Patent Document 3 discloses the production of oxacycloheptadec-10-en-2-one.

The Z-isomer of the oxacycloheptadec-8-en-2-one is registered under the CAS Number 123-69-3. The Z-isomer of the oxacycloheptadec-8-en-2-one is known as a natural product that is present in a plant natural fragrance "ambrette seed oil" in an amount of about 10%.

[Chemical Formula 1]

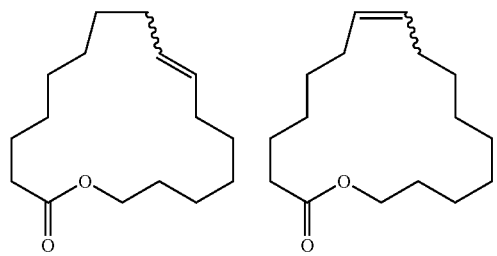

Oxacycloheptadec-10-en-2-one    Oxacycloheptadec-8-en-2-one

PRIOR ART DOCUMENTS

Patent Documents

Patent Document 1: JP 2017-517477 A
Patent Document 2: JP H11(1999)-293284 A
Patent Document 3: JP 2016-124868 A
Patent Document 4: WO 2016/005361

DISCLOSURE OF INVENTION

Problem to be Solved by the Invention

Musk is an important fragrance material that can be used widely, but is strongly animalic because it is an animal fragrance. Fresh fragrance notes with a feeling of cleanliness are preferred especially for toiletry products. In order to increase the degree of freedom in perfume blending, a fragrance composition with a mild musk fragrance note that is less animalic and that can easily be harmonized with other fragrance notes in a formulated fragrance has been demanded.

Therefore, it is an object of the present invention to provide a musk-like composition that is excellent in harmony with various other fragrances and that can create a distinctive fragrance effect when blended.

Means for Solving Problem

The present invention relates to a composition including a compound represented by General Formula (I), wherein a ratio of an E-isomer of the compound represented by General Formula (I) to a Z-isomer of the compound represented by General Formula (I) is E-isomer/Z-isomer=3/7 or more and 7/3 or less.

[Chemical Formula 2]

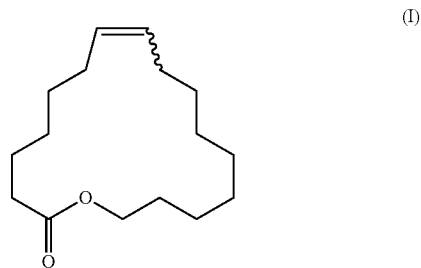 [SMILES: O=C1CCCCCC=CCCCCCCCCO1]

(I)

Effect of the Invention

The composition of the present invention is advantageous in that it is excellent in harmony with various other fragrances and can create a distinctive fragrance effect when blended.

DESCRIPTION OF THE INVENTION

In the compound represented by General Formula (I) of the present invention, the ratio of the E-isomer to the Z-isomer is E-isomer/Z-isomer=3/7 or more and 7/3 or less, preferably 4/6 or more and 7/3 or less, more preferably 5/5 or more and 7/3 or less, and further preferably more than 5/5 and 7/3 or less, from the viewpoint of achieving excellent harmony with various other fragrances and creating a distinctive fragrance effect when blended.

The composition of the present invention including the compound represented by General Formula (I) can be obtained, for example, by blending the E-isomer and the Z-isomer of the compound represented by General Formula (I) (hereinafter, also referred to as a "compound of General Formula (I)" or "compound (I)"), in the ratio of the E-isomer to the Z-isomer of E-isomer/Z-isomer=3/7 or more and 7/3 or less.

The E-isomer of the compound of General Formula (I) can be obtained by a conventionally known method. An exemplary method thereof is described in Facile synthesis of (E)-7-hexadecen-1,16-olide, J. In. Chem. Soc., Vol. 83, 1179-1180, 2006.

The Z-isomer of the compound of General Formula (I) can be obtained, for example, through ring-closing metathesis reaction of 9-decenyl-7-octenoate using a Z selective catalyst (Highly Active Ruthenium Metathesis Catalysts Exhibiting Unprecedented Activity and Z-Selectivity, J. Am. Chem. Soc., 135, 1276-1279, 2013).

The composition of the present invention preferably contains a fragrance other than the compound represented by General Formula (I). In the present invention, the content of the compound represented by Formula (I) in the composition is preferably 0.01 mass % or more, more preferably 0.1 mass % or more, further preferably 0.3 mass % or more, and still further preferably 1 mass % or more, while the content is preferably 99 mass % or less, more preferably 50 mass % or less, and further preferably 25 mass % or less, from the viewpoint of achieving excellent harmony with various other fragrances and creating a distinctive fragrance effect when blended.

The composition of the present invention includes the compound represented by General Formula (I), and the ratio of the E-isomer of the compound represented by General Formula (I) to the Z-isomer of the compound represented by General Formula (I) is E-isomer/Z-isomer=3/7 or more and 7/3 or less. By doing so, the composition can achieve excellent harmony with various other fragrances and create a distinctive fragrance effect when blended. Moreover, the composition of the present invention can contain, as fragrances other than the compound (I), other fragrance components in common use or formulated fragrances with a desired composition. The presence of the fragrance other than the compound (I) can provide the composition of the present invention with aromas of, e.g., a floral tone, a bouquet tone, a hyacinth tone, a geranium tone, a rose tone, a bergamot tone, an orchid tone, and a lily of the valley tone (muguet). In other words, it is preferable that the composition of the present invention further contains a fragrance other than the compound represented by General Formula (I).

In the composition of the present invention, examples of the other fragrances that can be used in combination with the compound (I) include alcohols, hydrocarbons, phenols, esters, carbonates, aldehydes, ketones, acetals, ethers, carboxylic acid, lactones other than the compound (I), nitriles, Schiff bases, and fragrance components such as natural essential oils and natural extracts.

Among them, alcohols, esters, aldehydes, ketones, ethers, carbonates, lactones, natural essential oils, and natural extracts are preferred.

In the present specification, the "plural notation" of each fragrance denotes a single compound or a mixture of two or more compounds.

Examples of the alcohols include aliphatic alcohols, terpene-based alcohols, aromatic alcohols, and other alcohols. Among them, aliphatic alcohols are preferred.

Examples of the terpene-based alcohols include linalool, citronellol, geraniol, nerol, terpineol, α-terpineol, dihydromyrcenol, farnesol, nerolidol, cedrol, menthol, borneol, and α-terpineol (p-menth-1-en-8-ol).

Examples of the aromatic alcohols include phenylethyl alcohol, benzyl alcohol, dimethyl benzyl carbinol, phenylethyl dimethyl carbinol, phenyl hexanol, AMBRINOL (1,2,3,4,4a,5,6,7-octahydro-2,5,5-trimethyl-naphthalene-2-ol), AMBRINOL 20T (trade name of Takasago International Coloration, 1,2,3,4,4a,5,6,7 octahydro-2,5,5-trimethyl naphthalene-2-ol), and INDOLENE 50BB (trade name of IFF, 7,7-bis(1H-indol-3-yl)-1,1,5-trimethyl-1-heptanol).

Examples of the aliphatic alcohols include cis-3-hexenol, 1-(2,2,6-trimethylcyclohexyl)-3-hexanol, AMBER CORE (trade name of Kao Corporation, 1-(2-tert-butylcyclohexyloxy)-2-butanol), SANDALMYSORE CORE (trade name of Kao Corporation, 2-methyl-4-(2,2,3-trimethyl-3-cyclopenten-1-yl)-2-buten-1-ol), MAGNOL (trade name of Kao Corporation, a mixture containing ethyl norbornyl cyclohexanol as a main component), UNDECAVERTOL (trade name of Givaudan, 4-methyl-3-decene-5-ol), isobornyl cyclohexanol, and POLYMEFLOR (trade name of Takasago International Corporation, 1-(2-methyl-2-propenyloxy)-2,2,4-trimethylpentan-3-ol).

Examples of the other alcohols include FLOROSA (trade name of Givaudan, chemical name: 4-methyl-2-(2-methylpropyl)tetrahydro-2H-4-pyranol), and decenol.

Examples of the hydrocarbons include limonene, α-pinene, β-pinene, terpinene, cedrene, longifolene, valencene, ocimene, AMBROTECH (trade name of Kao Corporation, dodecahydro-3a, 6,6,9a-tetramethylnaphtho[2,1-b]furan), FLOREX (trade name of Firmenich, 6-ethylideneoctahydro-5,8-methano-2H-1-benzopyran), and HABANOLIDE (trade name of Firmenich, cyclopentadecenolide).

Examples of the phenols include guaiacol, eugenol, isoeugenol, thymol, p-cresol, vanillin, and ethyl vanillin.

Examples of the esters include aliphatic carboxylic acid ester, aromatic carboxylic acid ester, and other carboxylic acid esters.

Examples of aliphatic carboxylic acids that form the aliphatic carboxylic acid ester include linear and branched carboxylic acids having 1 to 018 carbon atoms. Among them, carboxylic acids having 1 to 6 carton atoms such as formic acid, acetic acid, and propionic acid are important, and acetic acid is particularly important. Examples of aromatic carboxylic acids that form the aromatic carboxylic acid ester include benzoic acid, anisic acid, phenylacetic acid, cinnamic acid, salicylic acid, and anthranilic acid. Examples of alcohols that form aliphatic mid aromatic esters include linear and branched aliphatic alcohols having 1 to 5 carton atoms and the above-mentioned fragrance component alcohols.

Examples of the formate include linalyl formate, citronellyl formate, and geranyl formate.

Examples of the acetate include hexyl acetate, cis-3-hexenyl acetate, linalyl acetate, citronellyl acetate, geranyl acetate, neryl acetate, terpinyl acetate, nopyl acetate, bornyl acetate, isobornyl acetate, acetyl eugenol, acetyl isoeugenol, o-tert-butylcyclohexyl acetate, p-tert-butylcyclohexyl acetate, tricyclodecenyl acetate, benzyl acetate, phenylethyl acetate, styralyl acetate, cinnamyl acetate, dimethylbenzylcarbinyl acetate, phenylethyl phenyl acetate, 3-pentyltetrahydropyran-4-yl acetate, and p-cresyl phenyl acetate.

Examples of the propionate include citronellyl propionate, tricyclodecenyl propionate, allylcyclohexyl propionate, ethyl 2-cyclohexyl propionate, benzyl propionate, and styralyl propionate.

Examples of butyrate include citronellyl butyrate, dimethylbenzylcarbinyl n-butyrate, and tricyclodecenyl isobutyrate.

Examples of valerate include methyl valerate, ethyl valerate, butyl valerate, amyl valerate, benzyl valerate, and phenylethyl valerate. Examples of the hexanoate ester include methyl hexanoate, ethyl hexanoate, allyl hexanoate, linalyl hexanoate, and citronellyl hexanoate.

Examples of heptanoate include methyl heptanoate and allyl heptanoate.

Examples of nonenoate include methyl 2-nonenoate, ethyl 2-nonenoate, and ethyl 3-nonenoate.

Examples of the benzoate include methyl benzoate, benzyl benzoate, and 3,6-dimethyl benzoate.

Examples of the cinnamate include methyl cinnamate, benzyl cinnamate and phenylethyl cinnamate.

Examples of the salicylate include methyl salicylate, n-hexyl salicylate, cis-3-hexenyl salicylate, cyclohexyl salicylate, and benzyl salicylate.

Examples of brassylate include ethylene brassylate.

Examples of tiglate include geranyl tiglate, 1-hexyl tiglate, and cis-3-hexenyl tiglate.

Examples of jasmonate include methyl jasmonate and methyl dihydrojasmonate.

Examples of glycidate include methyl 2,4-dihydroxyethylmethylphenyl glycidate and 4-methylphenylethyl glycidate.

Examples of anthranilate include methyl anthranilate, ethyl anthranilate, and dimethyl anthranilate.

Examples of other esters include ETHYL SAFRANATE (trade name of Givaudan, ethyl dihydrocyclogenerate), POIRENATE (trade name of Kao Corporation, ethyl-2-cyclohexyl propionate), FRUITATE (trade name of Kao Corporation, ethyl tricyclo [5.2.1.0$^{2,6}$] decan-2-carboxylate), methyl jasmonate, MDJ (trade name of Kao Corporation, methyl dihydrojasmonate, methyl (2-pentyl-3-oxocyclopentyl)acetate), CYCLOHEXYL SALICYLATE (trade name of Kao Corporation), and I.P.M (isopropyl myristate).

Examples of the carbonates include LIFFAROME (trade name of IFF, cis-3-hexenyl methyl carbonate), JASMACYCLAT (trade name of Kao Corporation, methyl cyclooctyl carbonate), and FLORAMAT (trade name of Kao Corporation, ethyl-2-tert-butylcyclohexyl cartonate).

Examples of the aldehydes include n-octanal, n-nonanal, n-decanal, n-dodecanal, 2-methyl undecanal, 10-undecenal, citronellal, citral, hydroxycitronellal, TRIPLAL (trade name of IFF, 2,4-dimethyl-3-cyclohexene-1-carboxaldehyde), CYCLOVERTAL (trade name of Kao Corporation, dimethyl-3-cyclohexenyl-1-carboxaldehyde), benzaldehyde, phenylacetaldehyde, phenylpropylaldehyde, cinnamaldehyde, dimethyltetrahydrobenzaldehyde, BOURGEONAL (trade name of Givaudan, 3-(4-tert-butylphenyl)propanal), LYRAL (trade name of IFF, hydroxy myrac aldehyde), POLLENAL II (trade name of Kao Corporation, 2-cyclohexyl propanal), LILIAL (trade name of Givaudan, p-tert-butyl-α-methyl hydrocinnamaldehyde), p-isopropyl-α-methyl hydrocinnamaldehyde, FLORALOZONE (trade name of IFF, 3-(o-(and p-)ethylphenyl)-2,2-dimethylpropionaldehyde, α-amyl cinnamaldehyde, α-hexyl cinnamaldehyde, heliotropin, and HELIONAL (trade name of IFF, α-methyl-1,3-benzodioxole-5-propanal).

Examples of the ketones include methyl heptenone, dimethyl octenone, 3-octanone, hexylcyclopentanone, dihydrojasmone, VELOUTONE (trade name of Firmenich, 2,2,5-trimethyl-5-pentylcyclopentanone), NECTARYL (trade name of Givaudan, 2-(2-(4-methyl-3-cyclohexen-1-yl)propyl)cyclopentanone), ionone, β-ionone, methylionone, methylionone-G, γ-methylionone, damascone, α-damascone, β-damascone, δ-damascone, ISODAMASCONE (trade name of Symrise, 1-(2,4,4-trimethyl-2-cyclohexyl)-trans-2-butanone), damascenone, DYNASCONE (trade name of Firmenich, 1-(5,5-dimethyl-1-cyclohoxen-1-yl)-4-penten-1-one), irone, CASHMERAN (trade name of IFF, 1,2,3,5,6,7-hexahydro-1,1,2,3,3-pentamethyl-4H-inden-4-one), Iso E Super (trade name of IFF, 1-(1, 2, 3, 4, 5, 6,7,8-octahydro-2,3,8,8-tetramethyl-2-naphthalenyl-ethan-1-one), CALONE (trade name of Firmenich, 7-methyl-3,4-dihydro-2H-benzodioxepin-3-one), carvone, menthone, l-menthone, acetyl cedrene, isolongifolanone, nootkatone, benzyl acetone, raspberry ketone, benzophenone, TONALID (trade name of PFW, 6-acetyl-1,1,2,4,4,7-hexamethyl tetrahydronaphthalene), β-methyl naphthyl ketone, ethyl maltol, camphor, muscone (3-methyl cyclapentadecanone), l-muscone ((R)-3-methyl cyclopentadecanone), MUSCENONE (trade name of Firmenich, 3-methyl-5-cyclopentadecen-1-one), civetone, GLOBANONE (trade name of Symrise, 8-cyclohexadecenone), methyl nonyl ketone, cis-jasmone, FLORANTONE T (trade name of Takasago International Corporation, 1-(5,6,7,8-tetrahydronaphthalen-2-yl)ethanone), MUSK TM-II (trade name of SODA AROMATIC CO., LTD., 5-cyclohexadecen-1-one), MUSK Z-4 (trade name of IFF, (Z)-4-cyclopentadecen-1-one), and VELOUTONE (trade name of Firmenich, 2,5,5-trimethyl-2-pentylcyclopentanone). Among them, ionone, damascenone, Iso E Super, or γ-methylionone is preferred from the viewpoint of emphasizing floral sweetness when blended with other fragrances.

Examples of the acetals include acetaldehyde ethylphenylpropyl acetal, citral diethyl acetal, phenylacetaldehyde glyceryl acetal, ethyl acetoacetate ethylene glycol acetal, BOISAMBRENE FORTE (trade name of Kao evaporation), and TROENAN (trade name of Kao Corporation).

Examples of the ethers include ethyl linalool, cedryl methyl ether, estragole, anethole, β-naphthyl methyl ether, β-naphthyl ethyl ether, limonene oxide, rose oxide, nerol oxide, 1,8-cineole, rose furan, AMBROXAN (trade name of Kao Corporation, [3aR-(3aα, 5aβ, 9aα, 9bβ)]dodecahydro-3a, 6,6,9α-tetramethyl naphto[2,1-b]furan), HERBAVERT (trade name of Kao Corporation, 3,3,5-trimethylcyclohexyl ethyl ether), GALAXOLIDE (trade name of IFF, hexamethylhexahydrocyclopentabenzopyran), phenylacetaldehyde dimethyl acetal, and BOISAMBRENE FORTE (trade name of Kao Corporation, ethoxymethyl-cyclododecyl ether).

Examples of the carboxylic acids include benzoic acid, phenylacetic acid, cinnamic acid, hydrocinnamic acid, butyric acid, and 2-hexenoic acid.

Examples of the lactones other than the compound (I) include γ-decalactone, δ-decalactone, γ-valerolactone, γ-nonalactone, γ-undecalactone, δ-hexalactone, γ-jasmolactone, whisky lactone, coumarin, cyclopentadecenolide, cyclohexadecanolide, 11-oxahexadecanolide, and butylidenephthalide.

Examples of the nitriles include geranyl nitrile, citronellyl nitrile, and dodecanenitrile.

Examples of the Schiff bases include aurantiol and ligantral.

Examples of the natural essential oils and natural extracts include orange, lemon, lime, bergamot, vanilla, mandarin, peppermint, spearmint, lavender, chamomile, rosemary, eucalyptus, sage, basil, rose, rockrose, geranium, jasmine, ylang ylang, anise, clove, ginger, nutmeg, cardamom, cedar, cypress, vetiver, patchouli, lemongrass, labdanum, grapefruit, eucalyptus leaf oil, and guaiacwood oil.

The contents of the other fragrances each can be selected suitably depending on, for example, the type of formulated (blended) fragrances, the type and intensity of the intended odor, but are, in the composition, preferably 0.0001 mass % or more, more preferably 0.001 mass % or more, and preferably 99.99 mass % or less, more preferably 80 mass % or less. Furthermore, the total content of the other fragrances in the composition is preferably 5 mass % or more, more preferably 50 mass % or more, and preferably 99.99 mass % or less, more preferably 99.95 mass % or less.

The composition of the present invention can contain an odorless oil, as a base that allows the compound represented by General Formula (I) having a specific ratio of the E-isomer to the Z-isomer and other fragrant materials to be contained therein. Such an oil allows fragrance components to be mixed uniformly, to be easily mixed into a product, and to be easily provided with a suitable intensity of fragrance. Examples of the oil include: polyhydric alcohols such as ethylene glycol, propylene glycol, butylene glycol, and dipropylene glycol; esters such as isopropyl myristate, dibutyl adipate, and diethyl sebacate; hydrocarbons such as liquid paraffin and squalane; and surfactants such as polyoxyethylene alkyl ether and sorbitan fatty acid ester.

Among them, the oil is preferably polyhydric alcohol or ester, more preferably dipropylene glycol or isopropyl myristate from the viewpoint of the solubility of all the fragrance components. The content of the oil in the composition is preferably 0.01 mass % or more, more preferably 1 mass % or more, and further preferably 5 mass % or more, and preferably 95 mass % or less, more preferably 90 mass % or less, and further preferably 80 mass % or less.

The present invention further provides a cleanser containing the composition of the present invention, a cosmetic containing the composition of the present invention, and a fiber treating agent containing the composition of the present invention.

The cleanser of the present invention is preferably a body cleanser, a clothing cleanser, or a hard surface cleanser, more preferably a body cleanser or clothing cleanser, and further preferably a clothing cleanser.

Examples of the body cleanser include a skin cleanser, a hair cleanser, and a soap, and it is preferably a skin cleanser.

Examples of the hard surface cleanser include an all-purpose cleaner and a dish cleanser.

The fiber treating agent of the present invention is preferably a softener.

The cosmetic of the present invention is preferably a perfume, a milky lotion, a skin lotion, or a sunscreen, and more preferably a perfume.

The cleanser of the present invention preferably contains an anionic surfactant other than the composition of the present invention, and may further contain a nonionic surfactant, a pH adjuster, a viscosity modifier, a solvent, an oil, an antiseptic agent, water, or the like.

The fiber treating agent of the present invention preferably contains a cationic surfactant other than the composition of the present invention, and may further contain a pH adjuster, a solvent, an oil, an antiseptic agent, water, or the like.

The perfume of the present invention may contain a solvent, water, or the like, other than the composition of the present invention.

The composition of the present invention containing the compound represented by General Formula (I) having a specific ratio of the E-isomer to the Z-isomer is a musk-like composition, and as described above excellent in harmony with various other fragrances and can create a distinctive fragrance effect when blended. Therefore, as described above, the present invention relates to a method for using the composition as a fragrance-imparting component, specifically, a method for using the composition as a fragrance-imparting component for a composition, a cleanser, a cosmetic, or a fiber treating agent. The cleanser is preferably a body cleanser, a clothing cleanser, or a hard surface cleanser, more preferably a body cleanser or clothing cleanser, and further preferably a clothing cleanser. Examples of the body cleanser include a skin cleanser, a hair cleanser and a soap, and it is preferably a skin cleanser. Examples of the hard surface cleanser include an all-purpose cleaner and a dish cleanser. The cosmetic is preferably a perfume. The fiber treating agent is preferably a softener.

In the method for using the composition, the amount of the composition with respect to the cleanser, cosmetic, or softener is preferably 0.00001 mass % or more, more preferably 0.0001 mass % or more, and preferably 0.01 mass % or less, more preferably 0.001 mass % or less. By using the composition in this amount, it is possible to provide a product with an aroma of musk that is excellent in harmony with various fragrances and that can create a distinctive fragrance effect when blended.

In the method for using the composition, the amount of the composition with respect to the perfume is preferably 0.0001 mass % or more, more preferably 0.001 mass % or more, and preferably 0.1 mass % or less, more preferably 0.01 mass % or less. By using the composition in this amount, it is possible to provide a product with the aroma of musk that is excellent in harmony with various fragrances and that can create a distinctive fragrance effect when blended.

In the method for using the composition, a composition in which the composition is used as a fragrance-imparting component may contain an odorless oil. Such an oil is the same as that described with respect to the above-mentioned composition. In the method for using the composition, a composition in which the composition is used as a fragrance-imparting component may contain other fragrance components in common use or formulated fragrances with a desired composition as fragrances oilier than the composition (i.e., the composition containing the compound represented by General Formula (I) having a specific ratio of the E-isomer to the Z-isomer). The other fragrances are the same as those described with respect to the above-mentioned composition.

In the method for using the composition, a cleanser, a cosmetic, or a softener in which the composition is used as a fragrance-imparting component may contain an odorless oil. Such an oil is the same as that described with respect to the above-mentioned composition. In the method for using the composition, a cleanser, a cosmetic, or a softener in which the composition is used as a fragrance-imparting component may contain other fragrance components in common use or formulated fragrances with a desired composition as fragrances other than the compound represented by General Formula (I) having a specific ratio of the E-isomer to the Z-isomer. The other fragrances are the same as those described with respect to the above-mentioned composition.

With regard to the embodiments described above, the present invention further discloses the following compositions.

<1> A composition including a compound represented by General Formula (I), wherein a ratio of an E-isomer of the compound represented by General Formula (I) to a Z-isomer of the compound represented by General Formula (I) is E-isomer/Z-isomer=3/7 or more and 7/3 or less.

[Chemical Formula 3]

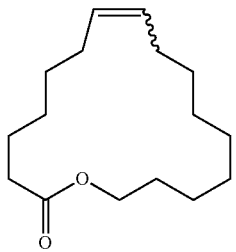

(I)

<2> The composition according to <1>, wherein the ratio of the E-isomer of the compound represented by General Formula (I) to the Z-isomer of the compound represented by General Formula (I) is E-isomer/Z-isomer=5/5 or more and 7/3 or less.

<3> The composition according to <1> or <2>, wherein the composition further includes a fragrance other than the compound represented by General Formula (I), and a content, of the compound represented by General Formula (I) is 0.01% by mass or more and 25% by mass or less.

<4> The composition according to <3>, wherein the fragrance other than the compound represented by General Formula (I) contains one or more of hydrocarbons, alcohols, phenols, aldehydes, ketones, acetals, ethers, esters, carbonates, lactones other than the compound (I), carboxylic acids, nitriles, Schiff bases, natural essential oils, or natural extracts.

<5> The composition according to <3> or <4>, wherein a ratio of the compound represented by General formula (I) to the fragrance other than the compound represented by General Formula (I) [the compound represented by General Formula (I)/the fragrance other than the compound represented by General Formula (I)] is 1/1000 or more, more preferably 5/1000 or more, and further preferably 10/1000 or more.

<6> The composition according to any one of <3> to <5>, wherein the ratio of the compound represented by General Formula (I) to the fragrance other than the compound represented by General Formula (I) [the compound represented by General Formula (I)/the fragrance other than the compound represented by General Formula (I)] is 100/1000 or less, more preferably 50/1000 or less, and further preferably 25/1000 or less.

<7> The composition according to any one of <3> to <6>, wherein the fragrance other than the compound represented by General formula (I) is ester, more preferably methyl dihydrojasmonate.

<8> The composition according to <7>, wherein a ratio of the compound represented by General Formula (I) to the fragrance of ester [the compound represented by General Formula (I)/the fragrance of ester] is 1/1000 or more, more preferably 10/1000 or more, and further preferably 20/1000 or more.

<9> The composition according to <7> or <8>, wherein the ratio of the compound represented by General Formula (I) to the fragrance of ester [the compound represented by General Formula (I)/the fragrance of ester] is 100/1000 or less, more preferably 50/1000 or less, and further preferably 40/1000 or less.

<10> The composition according to <3> or <4>, wherein the fragrance other than the compound represented by General Formula (I) is ether, more preferably hexamethylhexahydrocyclopentabenzopyran.

<11> The composition according to <10>, wherein a ratio of the compound represented by General Formula (I) to the fragrance of ether [the compound represented by General Formula (I)/the fragrance of other] is 1/1000 or more, more preferably 5/1000 or more, and further preferably 10/1000 or more.

<12> The composition according to <10> or <11>, wherein the ratio of the compound represented by General Formula (I) to the fragrance of ether [the compound represented by General Formula (I)/the fragrance of ether] is 100/1000 or less, more preferably 50/1000 or less, and further preferably 25/1000 or less.

<13> The composition according to <3> or <4>, wherein the fragrance other than the compound represented by General Formula (I) is alcohol, more preferably aromatic alcohol, and further preferably phenylethyl alcohol.

<14> The composition according to <13>, wherein a ratio of the compound represented by General Formula (I) to the fragrance of alcohol [the compound represented by General Formula (I)/the fragrance of alcohol] is 1/1000 or more, more preferably 5/1000 or more, and further preferably 10/1000 or more.

<15> The composition according to <13> or <14>, wherein the ratio of the compound represented by General Formula (I) to the fragrance of alcohol [the compound represented by General Formula (I)/the fragrance of alcohol] is 100/1000 or less, more preferably 50/1000 or less, and further preferably 25/1000 or less.

<16> The composition according to any one of <3> to <1.5> wherein the fragrance other than the compound represented by General Formula (I) is a musk-based fragrance other than the compound (I), more preferably one or more selected from GALAXOLIDE (trade name of IFF, hexamethylhexahydrocyclopentabenzopyran), HABANOLIDE (trade name of Firmenich, cyclopentadecenolide), 1-muscone ((R)-3-methyl cyclopentadecanone), muscone (3-methyl cyclopentadecanone), MUSK TM-II (trade name of SODA AROMATIC CO., LTD., 5-cyclohexadecen-1-ono), and MUSK Z-4 (trade name of IFF, (Z)-4-cyclopentadecen-1-one).

<17> The composition according to <16>, wherein a ratio of the compound represented by General Formula (I) to the musk-based fragrance [the compound represented by General Formula (I)/the musk-based fragrance] is 1/1000 or more, more preferably 5/1000 or more, and further preferably 10/1000 or more.

<18> The composition according to <16> or <17>, wherein the ratio of the compound represented by General Formula (I) to the musk-based fragrance [the compound represented by General Formula (I)/the musk-based fragrance] is 100/1000 or less, more preferably 50/1000 or less, and further preferably 25/1000 or less.

<19> A cleanser containing the composition according to any one of <1> to <18>.

<20> A cosmetic containing the composition according to any one of <1> to <18>.

<21> A fiber treating agent containing the composition according to any one of <1> to <18>.

<22> A method for using the composition according to <1> to <18> as a fragrance-imparting component.

<23> Use of the composition according to <1> to <18> as a fragrance-imparting component.

<24> A method for increasing fragrance intensity as a whole using the composition according to <1> to <18> as a fragrance-imparting component.

<25> Use of the composition according to <1> to <18> as a fragrance imparting component for increasing fragrance intensity as a whole.

<26> A method for imparting softness of musk using the composition according to <1> to <18> as a fragrant-imparting component.

<27> Use of the composition according to <1> to <18> as a fragrance-imparting component for imparting softness of musk.

EXAMPLES

Details of the measurement methods employed in the following examples and comparative examples are described together below.

[Identification of Compound]

Each compound obtained in the following production example was identified by matching data obtained by spectrum analyses using $^1$H-NMR and a gas chromatograph mass spectrometer (GC-MS) (model: GC-2010, manufactured by Shimadzu Corporation), with compound data disclosed by a known document or the like.

[Odor Evaluation]

Two experts who had an experience of perfume blending and fragrance evaluation determined the fragrance note and the intensity by a smelling strip method. In the evaluation, the tip of a smelling strip (fragrance test paper with a width of 6 mm and a length of 150 mm) was immersed about 5 mm in a sample.

With respect to the odor, fragrances that were sensed secondarily (secondary odors) were noted. In the evaluation of formulated fragrances, a fragrance not containing the composition of the present invention was used as a blank to evaluate the change in the fragrance note from the blank.

The E-isomer and the Z-isomer of the compound (I) used in the examples were produced in accordance with the production examples described below.

Here, the E-isomer of the compound (1) is (E)-oxacycloheptadec-8-en-2-one, and the Z-isomer of the compound (I) is (Z)-oxacycloheptadec-8-en-2-one.

Production Example 1

Synthetic method of a mixture containing oxacycloheptadec-8-en-2-one having an E-isomer/Z-isomer ratio of 91/9

Production Example 1

(a) Production of 9-decenyl-7-octenoate

In a flask, 9-decen-1-ol (manufactured by TOKYO CHEMICAL INDUSTRY CO., LTD., 2.2 g, 14.0 mmol) and 7-octenoic acid (manufactured by SIGMA-ALDRICH, 2.0 g, 1.4.0 mmol) were placed and then dissolved in dichloromethane (30 mL). Subsequently, 1-ethyl-3(3-dimethylaminopropyl)carbodiimide hydrochloride (3.2 g, 16.8 mmol) and N,N'-dimethylaminopyridine (171 mg, 1.4 mmol) were added to the flask. This was allowed to react under a nitrogen gas stream at room temperature for three hours. An ammonium chloride aqueous solution was added to the reaction solution obtained after the reaction was completed, which then was stirred. Thereafter, it was subjected to settled separation to extract an aqueous layer, and an oil layer was washed with saturated saline. Then sodium sulfate was added to the oil layer to dehydrate to dryness. After filtration thereof, dichloromethane was evaporated from the oil layer to obtain 9-decenyl-7-octenoate (3.9 g, 14.0 mmol) in a crude yield of 100%.

(b) Production of (E)-oxacycloheptadec-8-en-2-one

In a three-necked flask, 9-decenyl-7-octenoate (3.3 g, 11.8 mmol) obtained in the above process (a), dichloromethane (3 L), and a metathesis catalyst represented by formula below (trade name "Umicore M2" manufactured by Umicore Japan KK, 194 mg, 0.21 mmol) were placed and then heated to reflux (50° C.) under a nitrogen gas stream for 24 hours. Then 130 mg (0.14 mmol) of the metathesis catalyst represented by formula below was further added thereto, and stirring was continued for five hours. The reaction solution obtained after the reaction was completed was subjected to gas chromatography quantitative analysis and found to contain 2.0 g of oxacycloheptadec-8-en-2-one (E/Z=70/30, 7.9 mmol, yield 67%).

[Chemical Formula 4]

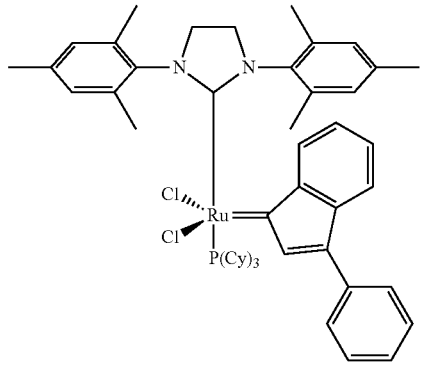

Dichloromethane was evaporated from the reaction solution and the residue was purified by silica gel column chromatography (eluent: n-hexane:ethyl acetate=95:5). Thus, 0.3 g of (E)-oxacycloheptadec-8-en-2-one (E/Z 91/9) was obtained.

Production Example 2

Synthetic Method of a Mixture Containing oxacycloheptadec-8-en-2-one Having an E-isomer/Z-isomer Ratio of 2/98

In a three-necked flask, 9-decenyl-7-octenoate (0.9 g, 3.2 mmol) obtained in Production Example 1 (a), dichloromethane (1.1 L), and a metathesis catalyst represented by formula below (manufactured by SIGMA-ALDRICH, 100 mg, 0.16 mmol) were placed and then heated to reflux (50° C.) under a nitrogen gas stream for 24 hours. Then 100 mg (0.16 mmol) of the metathesis catalyst represented by formula below was further added thereto, and stirring was continued for 24 hours. The reaction solution obtained after the reaction was completed was subjected to gas chromatography quantitative analysis and found to contain 0.4 g of (Z)-oxacycloheptadec-8-en-2-one (E/Z=2/98, 1.6 mmol, yield 49%).

[Chemical Formula 5]

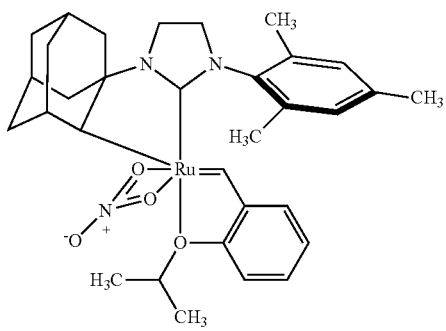

Dichloromethane was evaporated from the reaction solution and the residue was purified by silica gel column chromatography (eluent: n-hexane:ethyl acetate=99:1). Thus, 0.3 g of (Z)-oxacycloheptadec-8-en-2-one (E/Z=2/98) was obtained.

Examples 1 to 3 and Comparative Examples 1 to 4

Compositions having the constitution indicated in Table 1 were prepared using the mixture containing the compound (I) obtained in Production Example 1 (E-isomer/Z-isomer=91/9) and the mixture containing the compound (I) obtained in Production Example 2 (E-isomer/Z-isomer 2/98) and subjected to odor evaluation. Table 1 also shows the results of the odor evaluation.

[Chemical Formula 6]

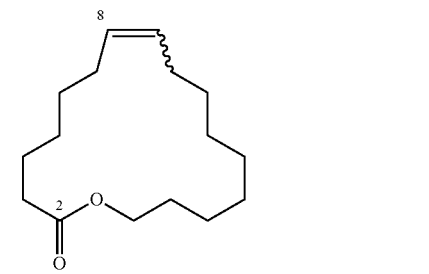

(I)

TABLE 1

| Fragrance material | Comp. Ex. 1 | Comp. Ex. 2 | Ex. 1 | Ex. 2 | Ex. 3 | Comp. Ex. 3 | Comp. Ex. 4 |
|---|---|---|---|---|---|---|---|
| Mixture containing compound (I) obtained in Production Example 1 (E-isomer/Z-isomer = 91/9) | 10.0 | 9.4 | 7.7 | 7.3 | 3.3 | 1.65 | — |
| Mixture containing compound (I) obtained in Production Example 2 (E-isomer/Z-isomer = 2/98) | — | 0.7 | 2.4 | 2.7 | 7.0 | 8.0 | 10.0 |
| Ratio of E-isomer/Z-isomer of compound (I) in composition | 91/9 | 85/15 | 70/30 | 67/33 | 30/70 | 17/83 | 2/98 |
| Result of odor evaluation | The fragrance was stagnant and did not spread. | The fragrance was slightly stronger than that of Comp. Ex. 1. | Musk with a stronger moist scent as compared with those of Comp. Exs. 1 and 4 and with aldehyde-like sweetness | Musk with a stronger moist scent as compared with those of Comp. Exs. 1 and 4 and with aldehyde-like sweetness | Musk with a stronger moist scent as compared with those of Comp. Exs. 1 and 4 and with aldehyde-like sweetness | Musk slightly sweeter than that of Comp. Ex. 4 | Musk with a moist scent and with a clear profile |

*Ex.: Example, Comp. Ex.: Comparative Example

Table 1 above indicates that the compositions of the comparative examples had the odor of slightly sweet musk, or the odor of musk with a moist scent and with a clear profile. Meanwhile, the compositions of the present invention had the odor of musk with a stronger moist scent as compared with those of Comparative Examples 1 and 4 and with aldehyde-like sweetness.

Examples 4 to 6 and Comparative Examples 5 to 9

Perfumes having the constitution indicated in Table 2 were prepared using the mixture containing the compound (I) obtained in Production Example 1 (E-isomer/Z-isomer=91/9) and the mixture containing the compound (I) obtained in Production Example 2 (E-isomer/Z-isomer=2/98). The obtained perfumes were subjected to odor evaluation. Table 8 shows the results of the odor evaluation.

TABLE 2

|  | Comp. Ex. 5 | Comp. Ex. 6 | Comp. Ex. 7 | Ex. 4 | Ex. 5 | Ex. 6 | Comp. Ex. 8 | Comp. Ex. 9 |
|---|---|---|---|---|---|---|---|---|
| Allyl heptanoate | 0.4 | 0.4 | 0.4 | 0.4 | 0.4 | 0.4 | 0.4 | 0.4 |
| AMBROXAN [1] | 3.0 | 3.0 | 3.0 | 3.0 | 3.0 | 3.0 | 3.0 | 3.0 |
| Coumarin | 3.0 | 3.0 | 3.0 | 3.0 | 3.6 | 3.0 | 3.0 | 3.6 |
| D.P.G [2] | 180.6 | 180.6 | 180.6 | 180.6 | 180.6 | 1806 | 180.6 | 180.6 |
| α-Damascone | 0.5 | 0.5 | 0.5 | 0.5 | 0.5 | 0.5 | 0.5 | 0.5 |
| γ-Decalactone | 1.5 | 1.5 | 1.5 | 1.5 | 1.5 | 1.5 | 1.5 | 1.5 |
| Ethyl linalool | 30.0 | 30.0 | 30.0 | 30.0 | 30.0 | 30.0 | 30.0 | 30.0 |
| Ethyl maltol | 0.3 | 0.3 | 0.3 | 0.3 | 0.3 | 0.3 | 0.3 | 0.3 |
| Ethylene brassylate | 60.0 | 60.0 | 60.0 | 60.0 | 60.0 | 60.0 | 60.0 | 60.0 |
| MDJ [3] | 270.0 | 270.0 | 270.0 | 270.0 | 270.0 | 270.0 | 270.0 | 270.0 |
| cis-3-Hexenol | 1.0 | 1.0 | 1.0 | 1.0 | 1.0 | 1.0 | 1.0 | 1.0 |
| cis-3-Hexenyl salicylate | 2.0 | 2.0 | 2.0 | 2.0 | 2.0 | 2.0 | 2.0 | 2.0 |
| Hexyl acetate | 1.0 | 1.0 | 1.0 | 1.0 | 1.0 | 1.0 | 1.0 | 1.0 |
| Hydroxycitronellal | 15.0 | 15.0 | 15.0 | 15.0 | 15.0 | 15.0 | 15.0 | 15.0 |
| β-Ionone | 25.0 | 25.0 | 25.0 | 25.0 | 25.0 | 25.0 | 25.0 | 25.0 |
| Iso E Super [4] | 120.0 | 120.0 | 120.0 | 120.0 | 120.0 | 120.0 | 120.0 | 120.0 |
| LIFFAROME [5] | 0.5 | 0.5 | 0.5 | 0.5 | 0.5 | 0.5 | 0.5 | 0.5 |
| LILIAL [6] | 45.0 | 45.0 | 45.0 | 45.0 | 45.0 | 45.0 | 45.0 | 45.0 |
| Methylionone-G | 45.0 | 45.0 | 45.0 | 45.0 | 45.0 | 45.0 | 45.0 | 45.0 |
| o-tert-Butylcyclohexyl acetate | 4.0 | 4.0 | 4.0 | 4.0 | 4.0 | 4.0 | 4.0 | 4.0 |
| Raspberry ketone | 6.0 | 6.0 | 6.0 | 6.0 | 6.0 | 6.0 | 6.0 | 6.0 |
| Styralyl acetate | 5.0 | 5.0 | 5.0 | 5.0 | 5.0 | 5.0 | 5.0 | 5.0 |
| VELOUTONE [7] | 0.2 | 0.2 | 0.2 | 0.2 | 0.2 | 0.2 | 0.2 | 0.2 |
| Damascenone | 1.0 | 1.0 | 1.0 | 1.0 | 1.0 | 1.0 | 1.0 | 1.0 |
| AMBER CORE [8] | 10.0 | 10.0 | 10.0 | 10.0 | 10.0 | 10.0 | 10.0 | 10.0 |
| Lemon oil | 40.0 | 40.0 | 40.0 | 40.0 | 40.0 | 40.0 | 40.0 | 40.0 |
| FLOROSA [9] | 40.0 | 40.0 | 40.0 | 40.0 | 40.0 | 40.0 | 40.0 | 40.0 |
| Mixture containing compound (I) obtained in Production Example 2 (E-isomer/Z-isomer = 2/98) | — | — | 0.7 | 2.4 | 2.7 | 7.0 | 8.0 | 10.0 |
| Mixture containing compound (I) obtained in Production Example 1 (E-isomer/Z-isomer = 91/9) | — | 10.0 | 9.4 | 7.7 | 7.3 | 3.3 | 1.65 | — |
| Total amount | 910.0 | 920.0 | 920.0 | 920.0 | 920.0 | 920.0 | 920.0 | 920.0 |
| Ratio of E-isomer/Z-isomer of compound (I) in composition | None | 91/9 | 85/15 | 70/30 | 67/33 | 30/70 | 17/83 | 2/98 |

* Numbers in Table indicate weight ratios.
[1] AMBROXAN (trade name of Kao Corporation, [3aR-(3aα,5aβ,9aα,9bβ)]-dodecahydro-3a,6,6,9a-tetramethyl naphto[2,1-b]furan)
[2] D.P.G: Dipropylene glycol
[3] MDJ (trade name of Kao Corporation, methyl dihydrojasmonate, methyl (2-pentyl-3-oxocyclopentyl)acetate)
[4] Iso E Super (trade name of IFF, 1-(1,2,3,4,5,6,7,8-octahydro-2,3,8,8-tetramethyl-2-napthalenyl)-ethan-1-one)
[5] LIFFAROME (trade name of IFF, cis-3-hexenyl methyl carbonate)
[6] LILIAL (trade name of Givaudan, p-tert-butyl-α-methyl hydrocinnamaldehyde)
[7] VELOUTONE (trade name of Firmenich, 2,2,5-trimethyl-5-pentylcyclopentanone)
[8] AMBER CORE (trade name of Kao Corporation, 1-(2-tert-butyl cyclohexyloxy)-2-butanol), SANDALMYSORE CORE (trade name of Kao Corporation)
[9] FLOROSA (trade name of Givaudan, chemical name: 4-methyl-2-(2-methylpropyl)tetrahydro-2H-4-pyranol)

TABLE 3

| | Ratio of E-isomer/Z-isomer | Evaluation results |
|---|---|---|
| Comp. Ex. 5 | None | Reference (formulated fragrances: sweet, fruity gourmand-like fragrance) |
| Comp. Ex. 6 | 91/9 | Sweetness of musk was imparted to the blank (Comp. Ex 5). |
| Comp. Ex. 7 | 85/15 | Sweetness of musk was imparted to the blank (Comp. Ex. 5), and the fragrance as a whole was harmonized. |
| Ex. 4 | 70/30 | Sweetness of musk was imparted to the blank (Comp. Ex. 5), and the fragrance as a whole was harmonized. Fragrance intensity as a whole was increased by aldehyde-like sweetness. |
| Ex. 5 | 67/33 | Sweetness of musk was imparted to the blank (Comp. Ex. 5), and the fragrance as a whole was harmonized. Fragrance intensity as a whole was increased by aldehyde-like sweetness. |
| Ex. 6 | 30/70 | Sweetness of musk was imparted to the blank (Comp. Ex. 5), and the fragrance as a whole was harmonized. Fragrance intensity as a whole was increased by aldehyde-like sweetness. |
| Comp. Ex. 8 | 17/83 | Sweetness of musk was imparted to the blank (Comp. Ex. 5), and the fragrance as a whole was harmonized. |
| Comp. Ex. 9 | 2/98 | Sweetness of musk was imparted to the blank (Comp. Ex. 5), and the fragrance as a whole was harmonized. |

Table 3 indicates that, as to the perfumes of the comparative examples, the sweetness of musk was imparted to the blank not containing the compound (I) (Comparative Example 5), and the fragrance as a whole was harmonized. Meanwhile, as to the perfumes of the present invention, the sweetness of musk was imparted to the blank not containing the compound (I) (Comparative Example 5), the fragrance as a whole was harmonized, and the fragrance intensity as a whole was increased by aldehyde-like sweetness.

Examples 7 to 9 and Comparative Examples 10 to 14

Perfumes having the constitution indicated in Table 4 were prepared using the mixture containing the compound (I) obtained in Production Example 1 (E-isomer/Z-isomer 91/9) and the mixture containing the compound (I) obtained in Production Example 2 (E-isomer/Z-isomer=2/98). The obtained perfumes were subjected to odor evaluation. Table 5 shows the results of the odor evaluation.

TABLE 4

| | Comp. Ex. 10 | Comp. Ex. 11 | Comp. Ex. 12 | Ex. 7 | Ex. 8 | Ex. 9 | Comp. Ex. 13 | Comp. Ex. 14 |
|---|---|---|---|---|---|---|---|---|
| AMBER CORE [1] | 1.42 | 1.42 | 1.42 | 1.42 | 1.42 | 1.42 | 1.42 | 1.42 |
| AMBRINOL [2] | 0.60 | 0.60 | 0.60 | 0.60 | 0.60 | 0.60 | 0.60 | 0.60 |
| AMBRINOL 20T [3] | 0.12 | 0.12 | 0.12 | 0.12 | 0.12 | 0.12 | 0.12 | 0.12 |
| AMBROTECH [4] | 0.36 | 0.36 | 0.36 | 0.36 | 0.36 | 0.30 | 0.36 | 0.36 |
| AMBROXAN [5] | 1.50 | 1.50 | 1.50 | 1.50 | 1.50 | 1.50 | 1.50 | 1.50 |
| BOISAMBRENE FORTE [6] | 0.08 | 0.08 | 0.08 | 0.08 | 0.08 | 0.08 | 0.08 | 0.08 |
| Cyclohexyl salicylate | 0.36 | 0.36 | 0.36 | 0.36 | 0.36 | 0.36 | 0.36 | 0.36 |
| D.P.G [7] | 428.87 | 428.87 | 428.87 | 428.87 | 428.87 | 428.87 | 428.87 | 428.87 |
| FLORANTONE T [8] | 0.04 | 0.04 | 0.04 | 0.04 | 0.04 | 0.04 | 0.04 | 0.04 |
| FLOREX [9] | 0.60 | 0.60 | 0.60 | 0.60 | 0.60 | 0.60 | 0.60 | 0.60 |
| GALAXOLIDE [10] | 520.00 | 520.00 | 520.00 | 520.00 | 520.00 | 520.00 | 520.00 | 520.00 |
| GLOBANONE [11] | 6.00 | 6.00 | 6.00 | 6.00 | 6.00 | 6.00 | 6.00 | 6.00 |
| HABANOLIDE [12] | 30.00 | 30.00 | 30.00 | 30.00 | 30.00 | 30.00 | 30.00 | 30.00 |
| INDOLENE 50BB [13] | 0.30 | 0.30 | 0.30 | 0.30 | 0.30 | 0.30 | 0.30 | 0.30 |
| 1-Muscone [14] | 0.04 | 0.04 | 0.04 | 0.04 | 0.04 | 0.04 | 0.04 | 0.04 |
| Muscone [15] | 0.60 | 0.60 | 0.60 | 0.60 | 0.60 | 0.60 | 0.60 | 0.60 |
| MUSK TM-II [16] | 1.20 | 1.20 | 1.20 | 1.20 | 1.20 | 1.20 | 1.20 | 1.20 |
| MUSK Z-4 [17] | 1.80 | 1.80 | 1.80 | 1.80 | 1.80 | 1.80 | 1.80 | 1.80 |
| POLYMEFLOR [18] | 0.11 | 0.11 | 0.11 | 0.11 | 0.11 | 0.11 | 0.11 | 0.11 |
| Mixture containing compound (I) obtained in Production Example 2 (E-isomer-Z-isomer = 2/98) | — | — | 0.7 | 2.4 | 2.7 | 7.0 | 8.0 | 10.0 |
| Mixture containing compound (I) obtained in Production Example 1 (E-isomer/Z-isomer = 91/9) | — | 10.0 | 9.4 | 7.7 | 7.3 | 3.3 | 1.65 | — |
| Total | 910.0 | 920.0 | 920.0 | 920.0 | 920.0 | 920.0 | 920.0 | 920.0 |
| Ration of E-isomer/isomer of compound (I) in composition | None | 91/9 | 85/15 | 70/30 | 67/33 | 30/70 | 17/83 | 2/98 |

* Numbers in Table indicate weight ratios.
[1] AMBER CORE (trade name of Kao Corporation, 1-(2-tert-butyl cyclohexyloxy)-2-butanol)
[2] AMBRINOL (trade name, 1,2,3,4,4a,5,6,7-octahydro-2,5,5-trimethyl-naphthalene-2-ol)
[3] AMBRINOL 20T (trade name of Takasago International Corporation, 1,2,3,4,4a,5,6,7-octahydro-2,5,5-trimethyl-naphthalene-2-ol)

TABLE 4-continued

|  | Comp. Ex. 10 | Comp. Ex. 11 | Comp. Ex. 12 | Ex. 7 | Ex. 8 | Ex. 9 | Comp. Ex. 13 | Comp. Ex. 14 |
|---|---|---|---|---|---|---|---|---|

[4] AMBROTECH (trade name of Kao Corporation, dodecahydro-3a,6,6,9a-tetramethylnaphto[2,1-b]furan)
[5] AMBROXAN (trade name of Kao Corporation, [3aR-(3aα,5aβ,9aα,9bβ)]-dodecahydro-3a,6,6,9a-tetramethyl naphto[2,1-b]furan)
[6] BOISAMBRENE FORTE (trade name of Kao Corporation, ethoxymethyl-cyclododecyl ether)
[7] D.P.G: Dipropylene gylcol
[8] FLORANTONE T (trade name of Takasago International Corporation, 1-(5,6,7,8-tetrahydronaphthalen-2-yl)ethanone)
[9] FLOREX (trade name of Firmenich, 6-ethylideneoctahydro-5,8-methano-2H-1-benzopyran)
[10] GALAXOLIDE (trade name of IFF, hexamethylhexahydrocyclopentabenzopyran)
[11] GLOBANONE (trade name of Symrise, 8-cyclohexadecenone)
[12] HABANOLIDE (trade name Firmenich, cyclopentadecenolide)
[13] INDOLENE 50BB (trade name of IFF, 7,7-bis(1H-indol-3-yl)-1,1,5-trimethyl-1-heptanol)
[14] 1-Muscone ((R)-3-methyl cyclopentadecanone)
[15] Muscone (3-methyl cyclopentadecanone)
[16] MUSK TM-II (trade name of SODA AROMATIC CO., LTD., 5-cyclohexadecen-1-one)
[17] MUSK Z-4 (trade name of IFF, (Z)-4-cyclopentadecen-1-one)
[18] POLYMEFLOR (trade name of Takasago International Corporation, 1-(2-methyl-2-propenyloxy)-2,2,4-trimethylpentan-3-ol)

TABLE 5

|  | Ratio of E-isomer/Z-isomer | Evaluation results |
|---|---|---|
| Comp. Ex. 10 | None | Reference (formulated fragrance: musk-like fragrance) |
| Comp. Ex. 11 | 91/9 | A musk scent was imparted to the blank (Comp. Ex. 10), but the fragrance was not harmonized and the intensity was weakened. |
| Comp. Ex. 12 | 85/15 | A feeling of clearness of musk was imparted to the blank (Comp. Ex. 10), but fragrance intensity was slightly weakened. |
| Ex. 7 | 70/30 | Softness of musk was imparted to the blank (Comp. Ex. 10), and the fragrance as a whole was harmonized. Depth and a feeling of cleanliness were imparted to the fragrance. |
| Ex. 8 | 67/33 | Softness of musk was imparted to the blank (Comp. Ex. 10), and the fragrance as a whole was harmonized. Depth, voluminousness and a feeling of cleanliness were imparted to the fragrance. |
| Ex. 9 | 30/70 | Sweetness of musk was imparted to the blank (Comp. Ex. 10), and the fragrance as a whole was harmonized. Whiteness of moist musk was felt. |
| Comp. Ex. 13 | 17/83 | Sweetness of musk was imparted to the blank (Comp. Ex. 10). The fragrance was gentler than that of Comp. Ex. A8 but stiff and slightly animalic, and did not harmonized. |
| Comp. Ex. 14 | 2/98 | An animalic scent of musk was imparted to the blank (Comp. Ex. 10), but the fragrance was slightly oily and stiff. |

Table 5 indicates that, as to the perfumes of the comparative examples, the sweetness of musk was imparted to the blank not containing the compound (I) (Comparative Example 10). Meanwhile, as to the perfumes of the present invention, the sweetness of musk was imparted to the blank not containing the compound (I) (Comparative Example 10), the fragrance as a whole was harmonized, and the depth, and a feeling of cleanliness were imparted to the fragrance.

Examples 10 to 12 and Comparative Examples 15 and 19

Perfumes having the constitution indicated in Table 6 were prepared using the mixture containing the compound (I) obtained in Production Example 1 (E-isomer/Z-isomer=91/9) and the mixture containing the compound (I) obtained in Production Example 2 (E-isomer/Z-isomer=2/98). The obtained perfumes were subjected to odor evaluation. Table 7 shows the results of the odor evaluation.

TABLE 6

|  | Comp. Ex. 15 | Comp. Ex. 16 | Comp. Ex. 17 | Ex. 10 | Ex. 11 | Ex. 12 | Comp. Ex. 18 | Comp. Ex. 19 |
|---|---|---|---|---|---|---|---|---|
| α-Pinene | 30.00 | 30.00 | 30.00 | 30.00 | 30.00 | 30.00 | 30.00 | 30.00 |
| α-Terpineol [1] | 10.00 | 10.00 | 10.00 | 10.00 | 10.00 | 10.00 | 10.00 | 10.00 |
| β-Pinene | 6.50 | 6.50 | 6.50 | 6.50 | 6.50 | 6.50 | 6.50 | 6.50 |
| Citronellol | 110.00 | 110.00 | 110.00 | 110.00 | 110.00 | 110.00 | 110.00 | 110.00 |
| Citronellyl acetate | 4.00 | 4.00 | 4.00 | 4.00 | 4.00 | 4.00 | 4.00 | 4.00 |
| Desenol | 1.50 | 1.50 | 1.50 | 1.50 | 1.50 | 1.50 | 1.50 | 1.50 |
| Eucalyptus oil | 1.00 | 1.00 | 1.00 | 1.00 | 1.00 | 1.00 | 1.00 | 1.00 |
| Eugenol | 4.00 | 4.00 | 4.00 | 4.00 | 4.00 | 4.00 | 4.00 | 4.00 |
| Geraniol | 50.00 | 50.00 | 50.00 | 50.00 | 50.00 | 50.00 | 50.00 | 50.00 |
| Geranyl acetate | 13.00 | 13.00 | 13.00 | 13.00 | 13.00 | 13.00 | 13.00 | 13.00 |

TABLE 6-continued

|  | Comp. Ex. 15 | Comp. Ex. 16 | Comp. Ex. 17 | Ex. 10 | Ex. 11 | Ex. 12 | Comp. Ex. 18 | Comp. Ex. 19 |
| --- | --- | --- | --- | --- | --- | --- | --- | --- |
| Guaiacwood oil | 85.00 | 85.00 | 85.00 | 85.00 | 85.00 | 85.00 | 85.00 | 85.00 |
| I.P.M [2] | 41.80 | 41.80 | 41.80 | 41.80 | 41.80 | 41.80 | 41.80 | 41.80 |
| Limonene | 1.50 | 1.50 | 1.50 | 1.50 | 1.50 | 1.50 | 1.50 | 1.50 |
| Linalool | 40.00 | 40.00 | 40.00 | 40.00 | 40.00 | 40.00 | 40.00 | 40.00 |
| Linalyl acetate | 55.00 | 55.00 | 55.00 | 55.00 | 55.00 | 55.00 | 55.00 | 55.00 |
| 1-Menthone | 1.20 | 1.20 | 1.20 | 1.20 | 1.20 | 1.20 | 1.20 | 1.20 |
| MDJ [3] | 120.00 | 120.00 | 120.00 | 120.00 | 120.00 | 120.00 | 120.00 | 120.00 |
| Nerol | 13.00 | 13.00 | 13.00 | 13.00 | 13.00 | 13.00 | 13.00 | 13.00 |
| Neryl acetate | 4.00 | 4.00 | 4.00 | 4.00 | 4.00 | 4.00 | 4.00 | 4.00 |
| Ocimane | 2.00 | 2.00 | 2.00 | 2.00 | 2.00 | 2.00 | 2.00 | 2.00 |
| Phenylethyl alcohol | 325.00 | 325.00 | 325.00 | 325.00 | 325.00 | 325.00 | 325.00 | 325.00 |
| Phenylethyl cinnamate | 5.00 | 5.00 | 5.00 | 5.00 | 5.00 | 5.00 | 5.00 | 5.00 |
| Rose oxid | 1.00 | 1.00 | 1.00 | 1.00 | 1.00 | 1.00 | 1.00 | 1.00 |
| TRIPLAL [4] | 10.00 | 10.00 | 10.00 | 10.00 | 10.00 | 10.00 | 10.00 | 10.00 |
| VELOUTONE [5] | 15.50 | 15.50 | 15.50 | 15.50 | 15.50 | 15.50 | 15.50 | 15.50 |
| Mixture containing compound (I) obtained in Production Example 2 (E-isomer/Z-isomer = 2/98) | — | — | 0.7 | 2.4 | 2.7 | 7.0 | 8.0 | 10.0 |
| Mixture containing compound (I) obtained in Production Example 1 (E-isomer/Z-isomer = 91/9 | — | 10.0 | 9.4 | 7.7 | 7.3 | 3.3 | 1.65 | — |
| Total amount | 910.0 | 920.0 | 920.0 | 920.0 | 920.0 | 920.0 | 920.0 | 920.0 |
| Ratio of E-isomer/Z-isomer of compund (I) in composition | None | 91/9 | 85/15 | 70/30 | 67/33 | 30/70 | 17/83 | 2/98 |

*Numbers in Table indicate weight ratios.
[1] α-Terpineol (2-(4-methylcyclohex-3-enyl)propan-2-ol)
[2] I.P.M (isopropyl myristate)
[3] MDJ (trade name of Kao Corporation, methyl dihydrojasmonate, methyl (2-pentyl-3-oxocyclopentyl)acetate)
[4] TRIPLAL (trade name of IFF, 2,4-dimethyl-3-cyclohexene-1-carboxaldehyde)
[5] VELOUTONE (trade name of Firmenich, 2,5,5-trimethyl-2-pentylcyclopentanone)

TABLE 7

|  | Ratio of E-isomer/Z-isomer | Evaluation results |
| --- | --- | --- |
| Comp. Ex. 15 | None | Reference (formulated fragrance: rose woody fragrance) |
| Comp. Ex. 16 | 91/9 | A feeling of clearness of musk was imparted to the blank (Comp. Ex. 15), but the voluminousness was insufficient. |
| Comp. Ex. 17 | 85/15 | A feeling of clearness and softness of musk were imparted to the blank (Comp. Ex. 15), but the voluminousness was slightly less than that of Ex. B1. |
| Ex. 10 | 70/30 | Sweetness and softness of musk were imparted to the blank (Comp. Ex. 15), and the fragrance as a whole was harmonized. A rose scent spread softly, and the voluminousness of the fragrance as a whole increased. |
| Ex. 11 | 67/33 | Sweetness and softness of musk were imparted to the blank (Comp. Ex. 15), and the fragrance as a whole was harmonized. A rose scent spread softly, and the voluminousness of the fragrance as a whole increased. |
| Ex. 12 | 30/70 | Sweetness of musk was imparted to the blank (Comp. Ex. 15), and the fragrance as a whole was harmonized. The profile of the whole fragrance became clearer, and the fresh green aide of rose became clearer. |
| Comp. Ex. 18 | 17/83 | Sweetness and an animalic scent of musk were imparted to fee blank (Comp. Ex. 15). The profile of the whole fragrance was more emphasized, but the fragrance was slightly stiff and not harmonized as a whole. |
| Comp. Ex. 19 | 2/98 | An animalic scent of musk was imparted to the blank (Comp. Ex. 15), but the fragrance as a whole was not harmonized. |

Table 7 indicates that, as to the perfumes of the comparative examples, the sweetness of musk was imparted to the blank not containing the compound (I) (Comparative Example 15). Meanwhile, as to the perfumes of the present invention, the sweetness of musk was imparted to the blank not containing the compound (I) (Comparative Example 15), a rose scent spread softly, and the voluminousness of the fragrance as a whole increased.

INDUSTRIAL APPLICABILITY

Since the composition of the present invention has a musk-tone odor useful as a fragrance, it can be used as a fragrance material. Moreover, since the composition of the present invention is excellent in harmony with various other fragrances and can create a distinctive fragrance effect when blended, it can be used as a fragrance-imparting component.

The invention claimed is:

1. A fragrance composition for imparting softness of musk, comprising a compound represented by the formula (I):

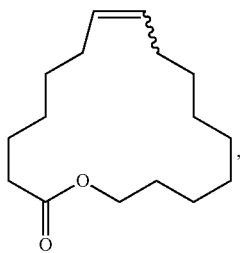

(I)

wherein a ratio of an E-isomer of the compound represented by the formula (I) to a Z-isomer of the compound represented by the formula (I), E-isomer/Z-isomer, is from 3/7 to 7/3 or less.

2. The composition according to claim 1, wherein the ratio of the E-isomer to the Z-isomer E-isomer/Z-isomer, is from 5/5 to 7/3.

3. The composition according to claim 1,
wherein the composition further comprises a fragrance other than the compound represented by the formula (I), and
a content of the compound represented by the formula (I) in the composition is from 0.01% by mass to 25% by mass.

4. The composition according to claim 3, wherein the fragrance other than the compound represented by the formula (I) is at least one selected form the group consisting of a hydrocarbon, alcohol, phenol aldehyde, ketone, acetal, ether, ester, carbonate, lactone other than the compound of the formula (I), carboxylic acid, nitrile, Schiff base, natural essential oil, and natural extract.

5. A cleanser, comprising the composition of claim 1.

6. A cosmetic, comprising the composition of claim 1.

7. A fiber treating agent, comprising the composition of claim 1.

8. A method for imparting fragrance, the method comprising adding the composition of claim 1 to a composition, a cleanser, a cosmetic, or a fiber treating agent, thereby imparting fragrance.

9. A method for increasing fragrance intensity, the method comprising adding the composition of claim 1 to a composition, a cleanser, a cosmetic, or a fiber treating agent, thereby increasing fragrance intensity.

10. A method for imparting softness of musk, the method comprising adding the composition of claim 1 to a composition, a cleanser, a cosmetic, or a fiber treating agent, thereby imparting softness of musk.

* * * * *